United States Patent
Qiao et al.

(10) Patent No.: US 9,301,763 B2
(45) Date of Patent: Apr. 5, 2016

(54) TILTABLE AND RESPOSITIONABLE ANVIL ASSEMBLY FOR STAPLER AND STAPLER COMPRISING THE SAME

(75) Inventors: Wei Qiao, Beijing (CN); Fanfeng He, Beijing (CN); Zhi Qu, Beijing (CN)

(73) Assignee: B.J.ZH.F. Panther Medical Equipment Co., Ltd., Beijing (CN)

( * ) Notice: Subject to any disclaimer, the term of this patent is extended or adjusted under 35 U.S.C. 154(b) by 673 days.

(21) Appl. No.: 13/582,762

(22) PCT Filed: Jul. 30, 2010

(86) PCT No.: PCT/CN2010/075578
§ 371 (c)(1),
(2), (4) Date: Sep. 5, 2012

(87) PCT Pub. No.: WO2011/109988
PCT Pub. Date: Sep. 15, 2011

(65) Prior Publication Data
US 2012/0325888 A1    Dec. 27, 2012

(30) Foreign Application Priority Data
Mar. 8, 2010    (CN) .......................... 2010 1 0120231

(51) Int. Cl.
*A61B 17/068* (2006.01)
*A61B 17/115* (2006.01)
*A61B 17/072* (2006.01)

(52) U.S. Cl.
CPC ........... *A61B 17/115* (2013.01); *A61B 17/1155* (2013.01); *A61B 2017/07257* (2013.01)

(58) Field of Classification Search
CPC .................................................... A61B 17/068
USPC ...................... 227/175.1, 176.1, 180.1, 181.1
See application file for complete search history.

(56) References Cited

U.S. PATENT DOCUMENTS

| 5,588,579 A  * | 12/1996 | Schnut et al. ............... 227/175.1 |
| 2008/0230581 A1* | 9/2008 | Marczyk et al. ........... 227/176.1 |
| 2010/0038401 A1* | 2/2010 | Milliman et al. .......... 227/175.1 |

FOREIGN PATENT DOCUMENTS

| CN | 2383476 Y | 6/2000 |
| CN | 2461494 Y | 11/2001 |
| CN | 2808065 Y | 8/2006 |
| CN | 2857837 Y | 1/2007 |
| EP | 2042108 A2 | 4/2009 |

OTHER PUBLICATIONS

International Search Report issued in parent PCT Application No. PCT/CN2010/075578, mailed on Dec. 9, 2010 (5 pages).

* cited by examiner

*Primary Examiner* — Nathaniel Chukwurah
(74) *Attorney, Agent, or Firm* — Wood, Herron & Evans, LLP

(57) ABSTRACT

A tiltable and repositionable anvil assembly for a stapler and a stapler comprising the same are provided. The tiltable and repositionable anvil assembly comprises: an anvil body having a connection portion for pivotable connection; a limitator; and a compression spring disposed between the anvil body and the limitator, in which in an operation of the stapler, the limitator is clamped at a clamping position between the connection portion of the anvil body and a connection portion of the stapler so as to keep the anvil body in a vertical state, and after the operation of the stapler, the limitator is moved away from the clamping position between the connection portion of the anvil body and the connection portion of the stapler, so that the anvil body is tiltable to a tilted state and the compression spring is compressed.

20 Claims, 3 Drawing Sheets

TILTABLE AND RESPOSITIONABLE ANVIL ASSEMBLY FOR STAPLER AND STAPLER COMPRISING THE SAME

FIELD

The present disclosure generally relates to a medical device, more particularly, to a tiltable and repositionable anvil assembly for a stapler and a stapler comprising the same.

BACKGROUND

A stapler is a medical device instead of a conventional manual suture in surgery. A tubular stapler is widely applied in human digestive tract surgery, for example, end-to-end or end-to-side anastomosis for the esophagus, stomach, duodenum, small intestine, etc. in a digestive tract. Especially in the case of relatively short operated connecting portion or unclear line of sight, a stapler needs to be used to achieve wound suturing. In surgery such as digestive tract reconstruction, a medical stapler is used to assist incision suturing, which has advantages of being simple in operation and rapid in suturing and substantially having no side effects and complications.

It is well known that a high-quality anastomosis technique is the key to determining whether a surgery is successful, while the success of the anastomosis technique is closely related to the structure of the used stapler. The security, usability and stability of an anastomosis device having a decisive influence on the success of the anastomosis technique are the key to successfully carrying out this type of surgery.

The medical stapler generally comprises an anvil assembly, a cartridge assembly, a connecting assembly, a firing assembly, a transmission assembly, a pivoting handle, a stationary handle and an adjusting assembly. Various improved medical disposable stapler are also known in the prior art. For example, Chinese invention patent 200710107833.8 discloses a disposable stapler having an automatic safety means. In this stapler, a pivoting handle located in the rear of the stapler is an automatic safety handle mounted on a stationary handle via an axle pin, and the axle pin is connected to a reset spring. By adopting such a disposition, the problem in unsuitably sending out a staple due to the fact that a doctor inadvertently touches the handle in operation may be solved. The entire contents of the above invention patent are incorporated herein by reference. For example, Chinese utility model patent 200820178201.0 discloses a disposable stapler having vent holes. The anvil at the head of the stapler is formed with one to three vent holes, thus eliminating the overhigh pressure in the anastomotic stoma, avoiding the impact on the stapling effect caused by the fact that the anastomotic stoma breaks, and avoiding the adverse impact on the postoperative tissue recovery of a human body. The entire contents of the above utility model patent are incorporated herein by reference.

After surgery, the entire stapler together with the anvil needs to be drawn out. In the case of minimally invasive surgery, the diameter of the anastomotic stoma is relatively small, so that staples of the stapler may easily fall off and the anastomotic stoma may break when the conventional stapler is taken out. To this end, Chinese invention patent application 201010112511.4 and Chinese utility model patent application 201020122097.0 of the applicant proposed a stapler having a tiltable anvil. After the anastomosis operation, the anvil can be tilted, and consequently the anvil may easily pass through smaller anastomotic stoma, thus reducing the risk of postoperative complications. The entire contents of the above invention patent application and the above utility model patent application are incorporated herein by reference.

However, in the traditional stapling surgery, the stapler is placed in a human tissue when a cap-shaped anvil is in a vertical state. This surgery has the following disadvantages. As the profile area of the stapler is large when the stapler is placed in the human tissue, it is difficult to place the anvil in the human tissue. Moreover, mucosal tissues in the lumen of the human tissue may be easily pushed in, but are not impaled when forming a purse and stapling, thus making it possible to bring various postoperative complications.

In order to overcome the above shortcomings in the prior art, there is a need for a stapler which has a small profile area when placed in and taken out of a human tissue and has a simple structure and a safe and convenient operation, so that the stapler may be easily placed in the human tissue and the anvil may easily pass through a small anastomotic stoma after the anastomosis. Therefore, the risk of postoperative complications may be reduced.

SUMMARY

In order to overcome the above shortcomings of a stapler in the prior art, a tiltable and repositionable anvil assembly for a stapler and a stapler comprising the same are provided.

According to a first aspect of the present disclosure, a tiltable and repositionable anvil assembly for a stapler is provided. The tiltable and repositionable anvil assembly comprises: an anvil body having a connection portion for pivotable connection; a limitator; and a compression spring disposed between the anvil body and the limitator, in which in an operation of the stapler, the limitator is clamped at a clamping position between the connection portion of the anvil body and a connection means of the stapler so as to keep the anvil body in a vertical state, and after the operation of the stapler, the limitator is moved away from the clamping position between the connection portion of the anvil body and the connection means of the stapler, so that the anvil body is tiltable to a tilted state and the compression spring is compressed.

Because the tiltable and repositionable anvil assembly according to this aspect of the present disclosure is pivotably connected, the stapler may be placed in a human tissue when the tiltable and repositionable anvil assembly is in a tilted state, so that the profile area of the stapler may be small so as not to cause the fact that mucosal tissues in the lumen of the human tissue is pushed in as the stapler is placed in the human tissue. After the stapler is placed in a predetermined position, the tiltable and repositionable anvil assembly may be conveniently repositioned to a vertical state by pushing the anvil body and under the action of the compression spring, so as to perform the stapling operation. Moreover, because the compression spring is compressed when the tiltable and repositionable anvil assembly is tilted, during the process of pushing the tiltable and repositionable anvil assembly to be repositioned, it is not required that the anvil body is pushed to a vertical state, it is merely required that the anvil body is pushed to a certain tilted position, and the tension of the compression spring may make the limitator be clamped at the clamping position, so as to finish the repositioning of the limitator. After the stapling and cutting of the stapler is finished, the annular knife continues advancing to push the limitator away from the clamping position between the tiltable and repositionable anvil assembly and the spring clamping pipe, so that the tiltable and repositionable anvil assembly may be tilted. As a result, the profile area of the entire stapler may be reduced, so that the stapler may be conveniently retracted from an anastomotic stoma, the anastomotic stoma and surrounding tissues thereof may be better protected, and the fact that staples are taken away when the stapler is retracted may be avoided. Therefore, the healing and recovery of the anastomotic stoma may be facilitated, thus ensuring the success of the surgery.

In an embodiment, a cutting ring is detachably disposed at a proximal end side of the limitator.

With the tiltable and repositionable anvil assembly according to this embodiment of the present disclosure, because the cutting ring is disposed at the proximal end side of the limitator, when the annular knife of the stapler is triggered in surgery, a "click" sound may be heard, which indicates that tissues on the cutting ring are effectively cut off and prompts that the stapler may be taken out of the anastomotic stoma safely and smoothly. In addition, the cutting ring may play the role of a cutting block, thus ensuring that the stapling is performed more uniformly. Moreover, the cutting ring may be conveniently replaced in the production and inspection process to repeat multiple tests, thus reducing the cost.

In an embodiment, the anvil body has two or more through holes.

With the tiltable and repositionable anvil assembly according to this embodiment of the present disclosure, on one hand, the through holes may play the role of vent holes to release the overhigh pressure in the anastomotic stoma; and on the other hand, these through holes may used as a seton, so that the doctor may deliver the stomach tube or the drainage tube to a target position incidentally when the doctor draws out the stapler from the anastomotic stoma after the anastomosis is finished.

According to a second aspect of the present disclosure, a stapler is provided. The stapler comprises: a tiltable and repositionable anvil assembly according to the first aspect of the present disclosure; and a connection means pivotably connected to the connection portion of the anvil body.

In an embodiment, the connection means comprises: a spring clamping pipe pivotably connected to the connection portion of the anvil body via a pin, and a torsion spring disposed at a connection position between the connection portion of the anvil body and the spring clamping pipe and coaxial with the pin, one end of the torsion spring is against the spring clamping pipe, and the other end of the torsion spring is against the tiltable and repositionable anvil assembly.

With the stapler according to this embodiment of the present disclosure, the pivotable connection between the tiltable and repositionable anvil assembly and the spring clamping pipe as one component of the stapler is achieved by using the pin, the torsion spring is disposed coaxially with the pin, one end of the torsion spring is against the spring clamping pipe, and the other end of the torsion spring is against the tiltable and repositionable anvil assembly. Therefore, after the stapling and cutting is finished by the stapler and the annular knife is retracted, the tiltable and repositionable anvil assembly may be automatically tilted, so that the operation may be very safe and convenient.

In an embodiment, a distal end of the spring clamping pipe is configured to be blunt.

With the stapler according to this embodiment of the present disclosure, the fact that the spring clamping pipe punctures the surrounding tissue may be avoided, thus further ensuring the safety of the surgery.

In an embodiment, a length of the spring clamping pipe is less than 40 mm.

The stapler according to this embodiment of the present disclosure may apply to a deep surgery.

In an embodiment, one or more positioning ribs are disposed on an external peripheral surface of the spring clamping pipe.

With the stapler according to this embodiment of the present disclosure, the tiltable and repositionable anvil assembly may be conveniently aligned to the spring clamping pipe, thus facilitating the operation of the doctor.

In an embodiment, one or more clamping reeds having an inward protuberance at a proximal end thereof are disposed on a peripheral surface of the spring clamping pipe.

With the stapler according to this embodiment of the present disclosure, the spring clamping pipe may be conveniently connected to a transmission assembly of the stapler.

In an embodiment, the spring clamping pipe is integrally formed.

The stapler according to this embodiment of the present disclosure may be easily manufactured and assembled, thus reducing the manufacturing cost of the stapler.

DETAILED DESCRIPTION

Embodiments of the present disclosure will be described below in detail with reference to the drawings. It should be noted that the drawings are merely schematic and are not necessarily drawn to scale, and shall not be construed to limit the scope of the present disclosure.

Figure 1:
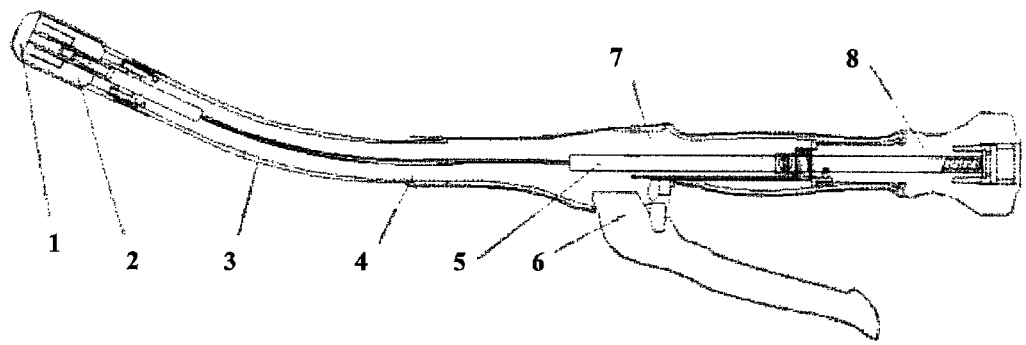
FIG. 1 is a schematic view showing a stapler according to an embodiment of the present disclosure.

FIG. 1 is a schematic view showing a stapler according to an embodiment of the present disclosure. As shown in FIG. 1, the stapler comprises a tiltable and repositionable anvil assembly 1, a cartridge assembly 2, a connecting assembly 3, a firing assembly 4, a transmission assembly 5, a pivoting handle 6, a stationary handle 7 and an adjusting assembly 8. For convenience, in the following description, the end of the stapler near the operator is called the proximal end, i.e., the end of the stapler in which the adjusting assembly 8 is located, and the end of the stapler away from the operator is called the distal end, i.e., the end of the stapler in which the tiltable and repositionable anvil assembly 1 is located.

In the stapler, the tiltable and repositionable anvil assembly 1 is connected to the transmission assembly 5 via a spring clamping pipe 12 at the proximal end of the tiltable and repositionable anvil assembly 1, the transmission assembly 5 is connected to the adjusting assembly 8 at the proximal end of the transmission assembly 5, and the firing assembly 4 extends in the connecting assembly 3 and the fixed handle 7 and is connected to the pivoting handle 6 at the proximal end of the firing assembly 4.

Figure 2:
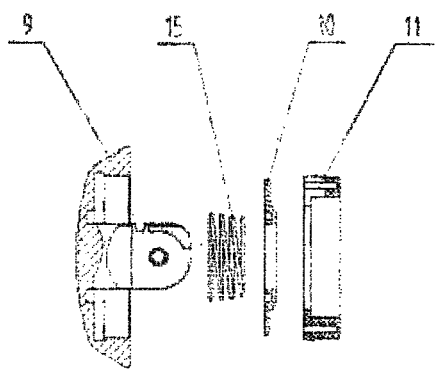
FIG. 2 is an exploded sectional view showing a tiltable and repositionable anvil assembly according to an embodiment of the present disclosure.
Figure 3:
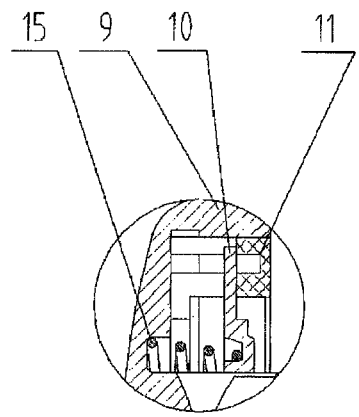
FIG. 3 is an enlarged partial sectional view showing a tiltable and repositionable anvil assembly according to an embodiment of the present disclosure, in which a cutting ring is joined to a limitator.

FIG. 2 is an exploded sectional view showing a tiltable and repositionable anvil assembly 1 according to an embodiment of the present disclosure. The tiltable and repositionable anvil assembly 1 may comprise a cap-shaped anvil body 9. In the embodiment shown in the drawings, the anvil body 9 may be provided with a ladder-shaped annular groove therein, and has a connection portion extending from the central portion of the anvil body 9 and having a through hole. The tiltable and repositionable anvil assembly 1 further comprises a limitator 10. Moreover, a compression spring 15 is disposed between the anvil body 9 and the limitator 10. When the tiltable and repositionable anvil assembly 1 is in a vertical state, i.e., in a state vertical to an axis of the following spring clamping pipe 12, the compression spring 15 may not be compressed, that is, the tension in the compression spring 15 is zero. The limitator 10 also has a through hole, and consequently may be fitted over the connection portion of the anvil body 9. The tiltable and repositionable anvil assembly 1 may be further formed with a detachably provided cutting ring 11 coupled to the limitator 10 at a proximal end side of the limitator 10. FIG. 3 is an enlarged partial sectional view showing a state in which the limitator 10 and the cutting ring 11 are assembled in the anvil body 9. It may be seen from FIG. 3 that in such a state, the limitator 10 is provided in the annular groove of the anvil body 9. It may also be further seen from FIGS. 2-3 that the compression spring 15 may be tapered, the distal end of the limitator 10 may be formed with an accommodating groove to accommodate one end of the compression spring 15, and the interior of the anvil body 9 may also be formed with an accommodating groove to accommodate the other end of the compression spring 15.

Figure 7:
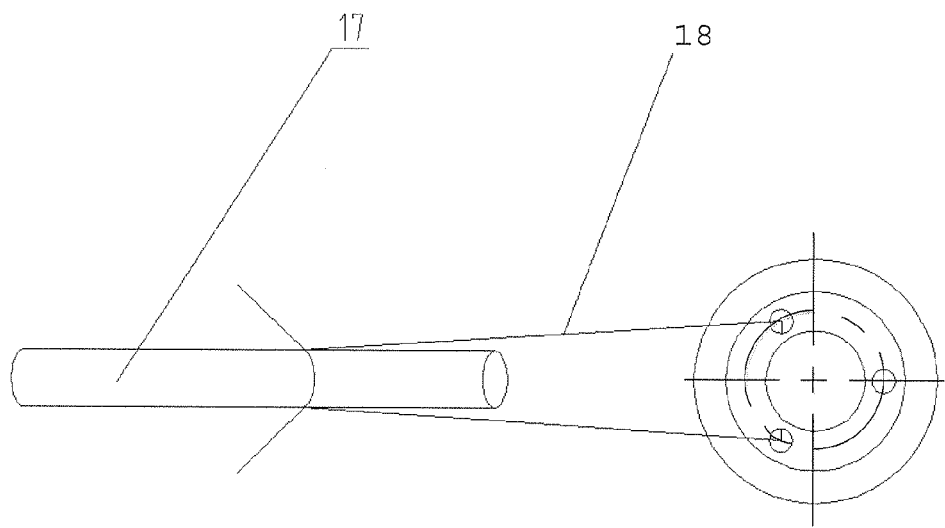
FIG. 7 is a schematic view schematically showing an anvil body having three through holes so as to achieve the seton function.

In addition, as shown in FIG. 7, the anvil body 9 may also be formed with three through holes. On one hand, these through holes may play the role of vent holes to release the overhigh pressure in an anastomotic stoma, thus avoiding the impact on the stapling effect caused by the fact that the anastomotic stoma breaks and facilitating the postoperative recovery of a patient. On the other hand, a surgical suture 18 may pass through two of these through holes, and two ends of the surgical suture 18 are joined to a stomach tube or a drainage tube 17 and knotted. In this way, when a doctor draws out the stapler from the anastomotic stoma after the anastomosis is finished, the doctor may deliver the stomach tube or the drainage tube 17 to a target position incidentally.

Figure 4:
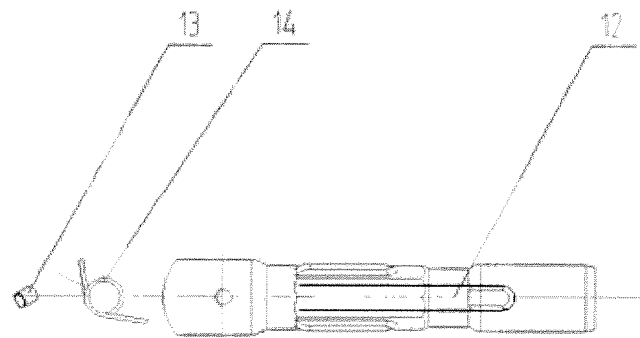
FIG. 4 is a schematic view showing a spring clamping pipe, a torsion spring and a pin for pivotably connection in a stapler according to an embodiment of the present disclosure.
Figure 5:
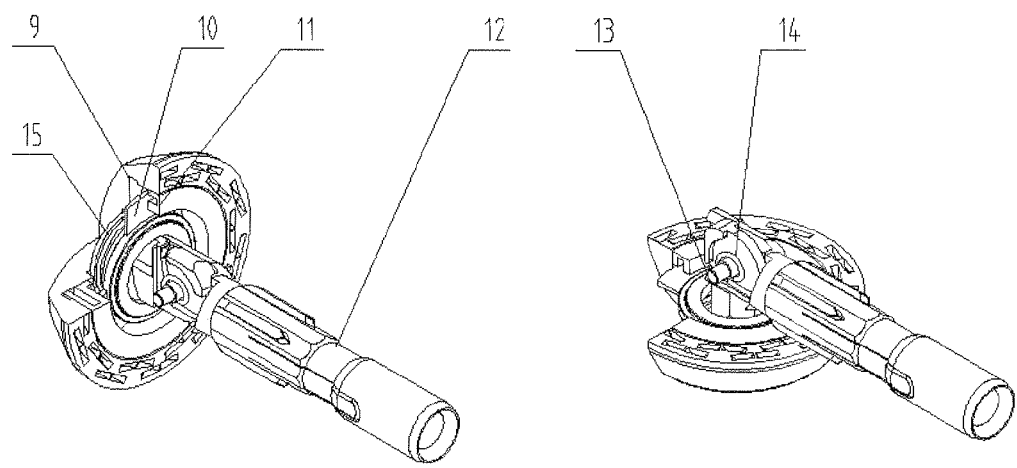
FIG. 5 is a partial sectional view showing a tiltable and repositionable anvil assembly in different states relative to a spring clamping pipe.

FIG. 4 shows a spring clamping pipe 12, and a torsion spring 14 and a pin 13 for pivotably connecting the spring clamping pipe 12 to the tiltable and repositionable anvil assembly 1 in a stapler according to an embodiment of the present disclosure. As shown in FIG. 5 which is a partial sectional view showing a tiltable and repositionable anvil assembly 1 in a vertical state and a tilted state, the spring clamping pipe 12 may comprise two lugs having holes at the distal end of the spring clamping pipe 12, and the pin 13 is inserted into and passes through the through hole of the connection portion of the anvil body 9 and the holes of the two lugs so as to pivotably connect the tiltable and repositionable anvil assembly 1 to the spring clamping pipe 12. Moreover, a torsion spring 14 may be disposed coaxially with the pin 13, one end of the torsion spring 14 is against the spring clamping pipe 12, and the other end of the torsion spring 14 is against the tiltable and repositionable anvil assembly 1. In addition, one or more clamping reeds may also be disposed on the peripheral surface of the spring clamping pipe 12, these clamping reeds may be uniformly distributed in a circumferential direction of the spring clamping pipe 12, and each clamping reed may have an inward protuberance at the proximal end thereof, thus facilitating the connection between the spring clamping pipe 12 and the transmission assembly 5.

The drawing out of the stapler is performed when the tiltable and repositionable anvil assembly 1 is in a tilted state, so that the distal end of the spring clamping pipe 12 may contact with a surrounding tissue. In this regard, the distal end of the spring clamping pipe 12 is configured to be blunt, thus avoiding the fact that the spring clamping pipe 12 punctures the surrounding tissue and further ensuring the safety of the surgery. In addition, in order to enable the stapler to apply to a deep surgery such as esophagus surgery, stomach surgery, etc. under an endoscope, a length of the spring clamping pipe 12 may be configured to be small, for example, is configured to be less than 40 mm.

As shown in the left view in FIG. 5, the limitator 10 is clamped at a clamping position between the tiltable and repositionable anvil assembly 1 and the spring clamping pipe 12. As a result, although the torsion spring 14 is disposed between the tiltable and repositionable anvil assembly 1 and the spring clamping pipe 12, the tiltable and repositionable anvil assembly 1 may be maintained in a vertical state relative to the spring clamping pipe 12. In such a state, the doctor may perform stapling, cutting, and other operations.

Figure 6:
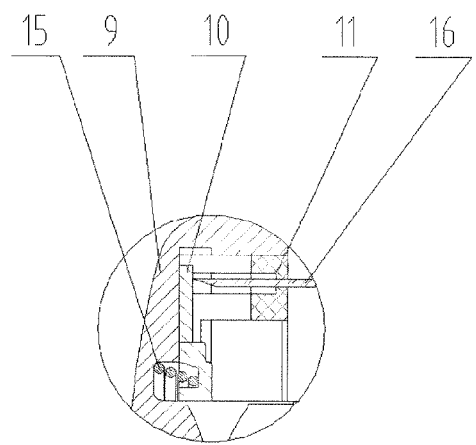
FIG. 6 is an enlarged partial sectional view showing a tiltable and repositionable anvil assembly according to an embodiment of the present disclosure, in which the cutting ring is cut off and the limitator is pushed to the top of the anvil body by an annular knife.

As shown in FIG. 6, after the doctor presses the pivoting handle 6 and triggers the firing assembly 4, the cutting ring 11 is cut off by an annular knife 16. At this time, a clear "click" sound may be made, so that the doctor may determine the success of the surgery conveniently. Moreover, the cutting ring 11 may play the role of a cutting block, thus ensuring that the stapling is performed more uniformly. After the cutting ring 11 is cut off, the annular knife 16 continues advancing to overcome the tension of the compression spring 15 and push the limitator 10 away from the clamping position between the tiltable and repositionable anvil assembly 1 and the spring clamping pipe 12, until the limitator 10 is against a distal top of the anvil body 9. At this time, once the annular knife 16 is retracted, the tiltable and repositionable anvil assembly 1 may be tilted, thus forming a state schematically shown in the right view in FIG. 5. In such a state, the compression spring 15 is compressed. In this way, when the stapler is taken out, the staples around the anastomotic stoma may not easily fall off, and the anastomotic stoma may not break.

The operation method of the stapler according to an embodiment of the present disclosure will be generally described below.

In surgery, the doctor first takes the stapler equipped with the tiltable and repositionable anvil assembly 1 according to an embodiment of the present disclosure out of an aseptic packaging bag. The adjusting assembly 8 is rotated to make a distance from the anvil body 9 to the distal end of the connecting assembly 3 be greater than or equal to 5 cm. Then, the limitator 10 is pressed toward the distal end of the anvil body 9 by overcoming the tension of the compression spring 15, so that the limitator 10 is moved away from a clamping position between the tiltable and repositionable anvil assembly 1 and a connection assembly of the stapler to achieve the tilting of the tiltable and repositionable anvil assembly 1. At this time, the compression spring 15 is compressed. The stapler is placed in a tissue which needs to be stapled in the state in which the tiltable and repositionable anvil assembly 1 is tilted. After the stapler is placed in the predetermined position, the anvil body 9 is pushed by a surgical clamp, and the limitator 10 is moved toward the proximal end of the anvil body 9 under the action of the tension of the compression spring 15 and clamped at the clamping position between the tiltable and repositionable anvil assembly 1 and the spring clamping pipe 12. Because the compression spring 15 is disposed between the anvil body 9 and the limitator 10, it is merely required that the anvil body 9 is pushed to a certain tilted position, it is not required that the anvil body 9 is pushed to a vertical state, and the tension of the compression spring 15 may make the limitator 10 be clamped at the clamping position between the tiltable and repositionable anvil assembly 1 and the spring clamping pipe 12, so that the anvil body 9 may be vertical to the spring clamping pipe 12. Therefore, such an operation is convenient and easy. In this way, the tiltable and repositionable anvil assembly 1 is in a state vertical to the axis of the spring clamping pipe 12 and is maintained in this state. At this time, the doctor may form a purse very conveniently. After the purse is formed, the adjusting assembly 8 is rotated to make the anvil body 9 against the distal end of the connecting assembly 3, and then the firing assembly 4 is triggered. After staples are correctly fired, the cutting ring 11 together with the tissue is cut off by the annular knife 16. Moreover, the annular knife 16 continues advancing to overcome the tension of the compression spring 15 and push the limitator 10 away from the clamping position between the tiltable and repositionable anvil assembly 1 and the spring clamping pipe 12. Then, the annular knife 16 is retracted, and the adjusting assembly 8 is rotated, so that the tiltable and repositionable anvil assembly 1 may be tilted. As a result, the stapler may be easily taken out.

Therefore, the stapler according to an embodiment of the present disclosure may be placed into a human tissue when the tiltable and repositionable anvil assembly 1 is in a tilted state; after placed in a predetermined position, the tiltable and repositionable anvil assembly 1 may be conveniently repositioned to a vertical state so as to perform the stapling; and after the stapling operation is finished, the tiltable and repositionable anvil assembly 1 may be tilted. That is, the stapler according to an embodiment of the present disclosure may have a simple structure and have a small profile area when placed into and taken out of the human tissue, so that the stapler may easily pass through a small anastomotic stoma after the anastomosis. Therefore, the operation may be secure and convenient.

Particular embodiments described herein are merely used to illustrate the spirit of the present disclosure by way of example. Various modifications, supplements or alternatives in a similar way may be made to the particular embodiments described herein by those skilled in the art, and the above individual features may be used alone or in a combination, without departing from the spirit of the present disclosure and going beyond the scope defined in the appended claims.

For example, in the illustrated embodiment, the pivotable connection between the tiltable and repositionable anvil assembly 1 and the spring clamping pipe 12 is achieved by a pin 13. However, it may be envisioned by those skilled in the art that other pivotable connection ways may be used, which may not depart from the scope of the present disclosure.

For example, in the illustrated embodiments, the limitator 10 is provided in the annular groove of the anvil body 9. However, it may be envisioned by those skilled in the art that any suitable way may be used to provide the limitator 10 in the anvil body 9, which may not depart from the scope of the present disclosure.

For example, in the illustrated embodiments, the anvil body 9 has three through holes. However, it may be envisioned by those skilled in the art that two or more through holes may be formed in the anvil body 9 according to practical requirements.

For example, in the illustrated embodiments, there are no particular limits on the shape and structure of the limitator 10, and any suitable shape and structure of the limitator 10 may be used by those skilled in the art, which may not depart from the scope of the present disclosure.

For example, there are no particular limits on the way of joining the limitator 10 to the cutting ring 11, and any suitable way may be used by those skilled in the art, which may not depart from the scope of the present disclosure.

For example, in the illustrated embodiments, corresponding portions of the anvil body 9 and the limitator 10 are grooved respectively to accommodate the compression spring 15. However, any suitable way may be used to accommodate the compression spring 15 by those skilled in the art, which may not depart from the scope of the present disclosure. Moreover, any suitable way may be used to avoid the loosening of the compression wring 15 by those skilled in the art, for example, the compression spring 15 may be fixedly joined to the anvil body 9 and/or the limitator 10 by a spot welding way or an interference fit way, which all fall into the scope of the present disclosure.

For example, in the illustrated embodiment, the compression spring 15 is tapered. However, it may be envisioned by those skilled in the art that the compression spring 15 having other shapes may be used, which all fall into the scope of the present disclosure.

What is claimed is:

1. A tiltable and repositionable anvil assembly for a stapler, comprising:
   an anvil body having a connection portion for pivotable connection;
   a limitator; and
   a compression spring disposed between the anvil body and the limitator,
   wherein in an operation of the stapler, the limitator is clamped at a clamping position between the connection portion of the anvil body and a connection portion of the stapler so as to keep the anvil body in a vertical state, and after the operation of the stapler, the limitator is moved away from the clamping position between the connection portion of the anvil body and the connection portion of the stapler, so that the anvil body is tiltable to a tilted state and the compression spring is compressed.

2. The tiltable and repositionable anvil assembly as set forth in claim 1, wherein a cutting ring is detachably disposed at a proximal end side of the limitator.

3. The tiltable and repositionable anvil assembly as set forth in claim 2, wherein the anvil body has two or more through holes.

4. The tiltable and repositionable anvil assembly as set forth in claim 1, wherein the anvil body has two or more through holes.

5. A stapler, comprising:
   a tiltable and repositionable anvil assembly comprising:
   an anvil body having a connection portion for pivotable connection;
   a limitator; and
   a compression spring disposed between the anvil body and the limitator,
   wherein in an operation of the stapler, the limitator is clamped at a clamping position between the connection portion of the anvil body and a connection portion of the stapler so as to keep the anvil body in a vertical state, and after the operation of the stapler, the limitator is moved away from the clamping position between the connection portion of the anvil body and the connection portion of the stapler, so that the anvil body is tiltable to a tilted state and the compression spring is compressed, and a connector pivotably connected to the connection portion of the anvil body.

6. The stapler as set forth in claim 5, wherein the connector comprises:

a spring clamping pipe pivotably connected to the connection portion of the anvil body via a pin, and a torsion spring disposed at a connection position between the connection portion of the anvil body and the spring clamping pipe and coaxial with the pin, one end of the torsion spring is against the spring clamping pipe, and the other end of the torsion spring is against the tiltable and repositionable anvil assembly.

7. The stapler as set forth in claim 6, wherein a distal end of the spring clamping pipe is configured to be blunt.

8. The stapler as set forth in claim 7, wherein a length of the spring clamping pipe is less than 40 mm.

9. The stapler as set forth in claim 7, wherein one or more positioning ribs are disposed on an external peripheral surface of the spring clamping pipe.

10. The stapler as set forth in claim 7, wherein one or more clamping reeds having an inward protuberance at a proximal end thereof are disposed on a peripheral surface of the spring clamping pipe.

11. The stapler as set forth in claim 6, wherein a length of the spring clamping pipe is less than 40 mm.

12. The stapler as set forth in claim 11, wherein one or more positioning ribs are disposed on an external peripheral surface of the spring clamping pipe.

13. The stapler as set forth in claim 11, wherein one or more clamping reeds having an inward protuberance at a proximal end thereof are disposed on a peripheral surface of the spring clamping pipe.

14. The stapler as set forth in claim 6, wherein one or more positioning ribs are disposed on an external peripheral surface of the spring clamping pipe.

15. The stapler as set forth in claim 14, wherein one or more clamping reeds having an inward protuberance at a proximal end thereof are disposed on a peripheral surface of the spring clamping pipe.

16. The stapler as set forth in claim 15, wherein the spring clamping pipe is integrally formed.

17. The stapler as set forth in claim 6, wherein one or more clamping reeds having an inward protuberance at a proximal end thereof are disposed on a peripheral surface of the spring clamping pipe.

18. The stapler as set forth in claim 6, wherein the spring clamping pipe is integrally formed.

19. The stapler as set forth in claim 5, wherein a cutting ring is detachably disposed at a proximal end side of the limitator.

20. The stapler as set forth in claim 5, wherein the anvil body has two or more through holes.

* * * * *